(12) United States Patent
Opsal et al.

(10) Patent No.: US 7,126,690 B2
(45) Date of Patent: Oct. 24, 2006

(54) MODULATED REFLECTANCE MEASUREMENT SYSTEM USING UV PROBE

(75) Inventors: Jon Opsal, Livermore, CA (US); Lena Nicolaides, Castro Valley, CA (US); Alex Salnik, Castro Valley, CA (US); Allan Rosencwaig, Danville, CA (US)

(73) Assignee: Therma-Wave, Inc., Fremont, CA (US)

( * ) Notice: Subject to any disclaimer, the term of this patent is extended or adjusted under 35 U.S.C. 154(b) by 469 days.

(21) Appl. No.: 10/659,626

(22) Filed: Sep. 10, 2003

(65) Prior Publication Data

US 2004/0104352 A1    Jun. 3, 2004

Related U.S. Application Data

(60) Provisional application No. 60/413,094, filed on Sep. 24, 2002, provisional application No. 60/413,229, filed on Sep. 23, 2002.

(51) Int. Cl.
G01N 21/55    (2006.01)

(52) U.S. Cl. .................. 356/445; 356/447

(58) Field of Classification Search ........ 356/445–448, 356/432, 51; 250/372, 358.1
See application file for complete search history.

(56) References Cited

U.S. PATENT DOCUMENTS

| | | | |
|---|---|---|---|
| 4,522,510 A | 6/1985 | Rosencwaig et al. | 374/7 |
| 4,634,290 A | 1/1987 | Rosencwaig et al. | 374/5 |
| 4,636,088 A | 1/1987 | Rosencwaig et al. | 374/5 |
| 4,710,030 A * | 12/1987 | Tauc et al. | 356/432 |
| 5,034,611 A | 7/1991 | Alpern et al. | 250/372 |
| 5,074,669 A | 12/1991 | Opsal | 356/445 |
| 5,298,970 A | 3/1994 | Takamatsu et al. | 356/349 |
| 5,633,711 A * | 5/1997 | Nelson et al. | 356/318 |
| 5,978,074 A | 11/1999 | Opsal et al. | 356/72 |
| 6,268,916 B1 | 7/2001 | Lee et al. | 356/369 |
| 6,411,390 B1 | 6/2002 | Nikoonahad et al. | 356/502 |

* cited by examiner

Primary Examiner—Layla G. Lauchman
(74) Attorney, Agent, or Firm—Stallman & Pollock LLP

(57) ABSTRACT

A modulated reflectance measurement system includes lasers for generating an intensity modulated pump beam and a UV probe beam. The pump and probe beams are focused on a measurement site within a sample. The pump beam periodically excites the measurement site and the modulation is imparted to the probe beam. For one embodiment, the wavelength of the probe beam is selected to correspond to a local maxima of the temperature reflectance coefficient of the sample. For a second embodiment, the probe laser is tuned to either minimize the thermal wave contribution to the probe beam modulation or to equalize the thermal and plasma wave contributions to the probe beam modulation.

11 Claims, 4 Drawing Sheets

MODULATED REFLECTANCE MEASUREMENT SYSTEM USING UV PROBE

PRIORITY CLAIM

The present application claims priority to U.S. Provisional Patent Application Ser. No. 60/413,229, filed Sep. 23, 2002 and U.S. Provisional Patent Application Ser. No. 60/413,094, filed Sep. 24, 2002, both of which are incorporated in this document by reference.

TECHNICAL FIELD

The subject invention relates generally to optical methods for inspecting and analyzing semiconductor wafers and other samples. In particular, the subject invention relates to methods for increasing the accuracy and flexibility of systems that use photo modulated reflectivity to analyze semiconductor wafers.

BACKGROUND OF THE INVENTION

There is a great need in the semiconductor industry for metrology equipment that can provide high resolution, non-destructive evaluation of product wafers as they pass through various fabrication stages. In recent years, a number of products have been developed for the nondestructive evaluation of semiconductor samples. One such product has been successfully marketed by the assignee herein under the trademark Therma-Probe. This device incorporates technology described in the following U.S. Pat. Nos. 4,634,290; 4,646,088; 5,854,710; 5,074,669 and 5,978,074. Each of these patents is incorporated herein by reference.

In the basic device described in the patents, an intensity modulated pump laser beam is focused on the sample surface for periodically exciting the sample. In the case of a semiconductor, thermal and plasma waves are generated in the sample that spread out from the pump beam spot. These waves reflect and scatter off various features and interact with various regions within the sample in a way that alters the flow of heat and/or plasma from the pump beam spot.

The presence of the thermal and plasma waves has a direct effect on the reflectivity at the surface of the sample. As a result, subsurface features that alter the passage of the thermal and plasma waves have a direct effect on the optical reflective patterns at the surface of the sample. By monitoring the changes in reflectivity of the sample at the surface, information about characteristics below the surface can be investigated.

In the basic device, a second laser is provided for generating a probe beam of radiation. This probe beam is focused collinearly with the pump beam and reflects off the sample. A photodetector is provided for monitoring the power of reflected probe beam. The photodetector generates an output signal that is proportional to the reflected power of the probe beam and is therefore indicative of the varying optical reflectivity of the sample surface. The output signal from the photodetector is filtered to isolate the changes that are synchronous with the pump beam modulation frequency. A lock-in detector is typically used to measure both the in-phase (I) and quadrature (Q) components of the detector output. The two channels of the output signal, namely the amplitude $A^2 = I^2 + Q^2$ and phase $\Theta = \arctan(I/Q)$ are conventionally referred to as the photomodulated reflectivity (PMR) or Thermal Wave (TW) signal amplitude and phase, respectively.

Dynamics of the thermal- and carrier plasma-related components of the total PMR signal in a semiconductor is given by the following general equation:

$$\frac{\Delta R}{R} = \frac{1}{R}\left(\frac{\partial R}{\partial T}\Delta T_0 + \frac{\partial R}{\partial N}\Delta N_0\right)$$

where $\Delta T_0$ and $\Delta N_0$ are the temperature and the carrier plasma density at the surface of a semiconductor, R is the reflectance, dR/dT is the temperature reflectance coefficient and dR/dN is the carrier reflectance coefficient. For silicon, dR/dT is positive in the visible and near-UV part of the spectrum while dR/dN remains negative throughout the entire spectrum region of interest. The difference in sign results in destructive interference between the thermal and plasma waves and decreases the total PMR signal. The magnitude of this effect depends on the nature of a semiconductor sample and on the parameters of the photothermal system, especially on the pump and probe beam wavelengths.

In the early commercial embodiments of the TP device, both the pump and probe laser beams were generated by gas discharge lasers. Specifically, an argon-ion laser emitting a wavelength of 488 nm was used as a pump source. A helium-neon laser operating at 633 nm was used as a source of the probe beam. Lore recently, solid state laser diodes have been used and are generally more reliable and have a longer lifetime than gas discharge lasers. In the current commercial embodiment, the pump laser operates at 780 nm while the probe laser operates at 670 nm.

In practice, the use of the visible spectrum for both pump and probe beams has proven to be effective for a broad range of practical applications. Alternatively, U.S. Pat. Ser. No. 5,034,611 discloses a PMR system having a 488 nm pump beam and a beam probe in the UV range of 200 through 345 nm. That particular combination is believed to be an effective tool for measuring implantation doses above $10^{15}$ cm$^{-2}$ at relatively shallow depth (i.e., approximately 10 nm).

As may be appreciated, it is entirely possible to construct PMR systems that operate at probe and pump wavelengths that differ from the systems described above. As will be described below, there are applications that benefit from these alternate configurations. This is particularly true for applications that involve relatively high temperature reflectance coefficients.

SUMMARY

The present invention provides a modulated reflectance measurement system with the capability to make measurements using a probe beam in the near-UV and UV parts of the spectrum. The measurement system includes a probe laser and a pump laser, each producing monochromatic light at a different spectrum. A modulator causes the pump laser to have an intensity modulated output, referred to as the pump beam. The probe laser produces an output that is typically non-modulated (i.e., constant intensity). This output is referred to as the probe beam.

The output of the probe laser and the output of the pump laser are joined into a collinear beam using a laser diode power combiner. An optical fiber transports the now collinear probe and pump beams from the laser diode power combiner to a lens or other optical device for collimation. Once collimated, the collinear beam is focused on a sample by an objective lens.

A reflected portion of the collinear probe and pump beams is redirected by a beam splitter towards a detector. The detector measures a portion of the probe beam which is reflected by the sample and forwards a corresponding signal to a filter. The filter typically includes a lock-in amplifier that uses the output of the detector, along with the output of the modulator to produce quadrature (Q) and in-phase (I) signals for analysis. A processor typically converts the Q and I signals to amplitude and/or phase values to analyze the sample. In other cases, the Q and I signals are used directly.

For one implementation, the probe laser is configured to operate in the 400–405 nm wavelength range. At that spectral range, the difference between the temperature reflectance coefficient and the carrier reflectance coefficient is maximized. This increases the signal measured by the detector when measuring samples with thermally-dominated modulated reflectance signals. For a second implementation, the probe laser operates in the 360 nm wavelength range. At that spectral range, both the temperature and carrier plasma reflectance coefficients have the same (negative) sign leading to a constructive interference between the thermal and carrier plasma wave contributions to the total PMR signal. Once again, this increases the signal measured by the detector when measuring samples with thermally-dominated modulated reflectance signals.

A third implementation of the modulated reflectance measurement system uses a wavelength tunable probe laser. The probe laser operates at a nominal or central wavelength in the UV range and is tunable to operate at shorter or longer wavelengths. To analyze a sample, an initial site is measured within the sample. At the initial site, the probe laser is tuned to minimize the thermal wave contribution to the total PMR signal. At subsequent sites, the probe laser wavelength is held constant and the PMR signal re-measured. Differences in the measured signal indicate differences in sample characteristics. This technique is effective for samples that exhibit a thermally-dominated PMR signal.

For samples where the PMR signal is not thermally-dominated, the probe laser is tuned to equalize the contributions from the thermal wave and carrier plasma to the total PMR signal. This allows the modulated reflectance measurement system to operate in the plasma-to-thermal transition region which maximizes the sensitivity of PMR phase measurements.

DETAILED DESCRIPTION OF THE PREFERRED EMBODIMENTS

Figure 1:
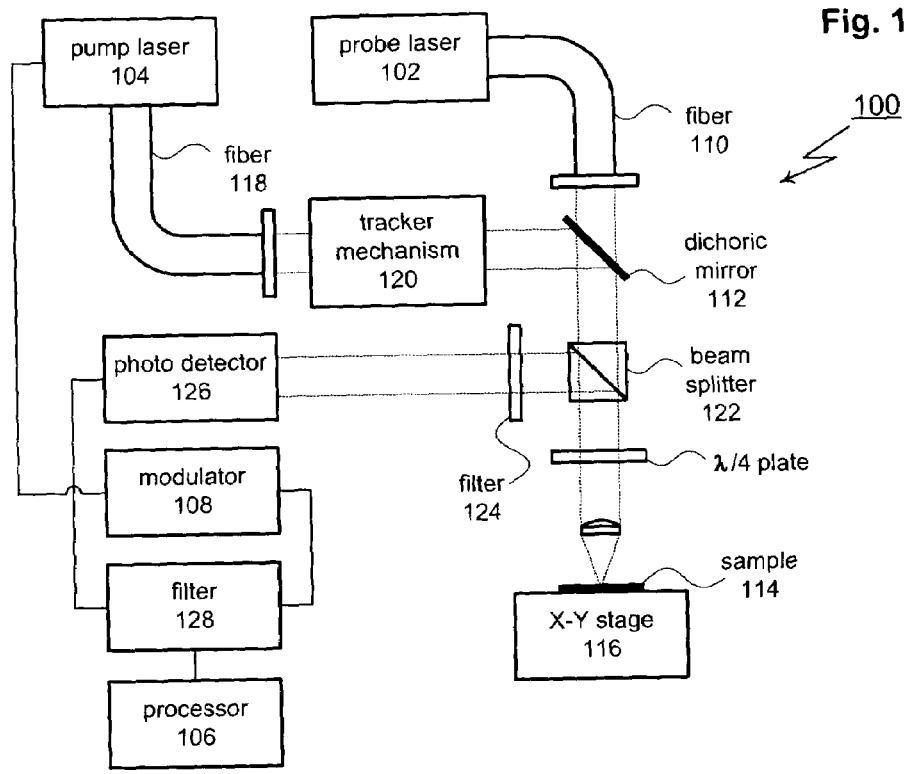
FIG. 1 is a block diagram of a modulated reflectance measurement system as provided by an embodiment of the present invention.

The present invention provides a modulated reflectance measurement system with the capability to make measurements using a probe beam in the near-UV and UV spectrum. The modulated reflectance measurement system is adaptable for use with fixed or tunable wavelength probe beams. One possible implementation for the modulated reflectance measurement system is shown in FIG. 1 and designated 1001 As shown, modulated reflectance measurement system 100 includes a probe laser 102 and a pump laser 104. Each laser 102, 104 is typically monochromatic and each laser 102, 104 typically operates at a different spectrum. Lasers 102, 104 are generally diode-based or diode-pumped semiconductor lasers. Solid state laser diodes are available that have outputs throughout the entire visible spectrum as well as in the infrared and near UV. Lasers 102, 104 are controlled by a processor 106 and a modulator 108. Modulator 108 causes pump laser 104 to have an intensity modulated output, referred to as the pump beam. Probe laser 102 produces an output that is typically non-modulated (i.e., constant intensity). This output is referred to as the probe beam.

As the probe beam leaves probe laser 102, it is preferably collected by an optical fiber 110. Optical fiber 110 is typically single mode and directs the probe beam through a dichroic mirror 112 towards a sample 114. Sample 114 is positioned on an X-Y stage 116 allowing sample to be moved in translation relative to the probe beam. As the pump beam leaves pump laser 104, it is preferably collected by a second optical fiber 118. Optical fiber 118 is typically single mode and directs the pump beam to a tracking mechanism 1201 After leaving tracking mechanism 120, the pump beam is redirected by dichroic mirror 112. The redirection aligns the pump beam to be collinear with the probe beam as the probe beam travels towards sample 114.

After striking sample 114, the reflected pump and probe beam are redirected by a beam splitter 122 through a filter 124 and towards a detector 126. Filter 124 removes the pump beam component of the reflected beams, while allowing the probe beam component to pass uninhibited. Detector 126 provides an output signal that is proportional to the power of the reflected probe beam. Detector 126 is arranged to be underfilled so that its output can be insensitive to any changes in beam diameter or position. In the preferred embodiment, detector 126 is a quad cell generating four separate outputs. When used to measure reflected beam power, the output of all four quadrants are summed. As described in U.S. Pat. No. 5,978,074, the apparatus can also be operated to measure beam deflection. In the latter case, the output of one adjacent pair of quadrants is summed and subtracted from the sum of the remaining pair of quadrants.

The output of detector 126 is passed to a filter 128. Filter 128 typically includes a lock-in amplifier that uses the output of detector 126, along with the output of modulator 108 to produce quadrature (Q) and in-phase (I) signals for analysis. Processor 106 typically converts the Q and I signals to amplitude and/or phase values to analyze the sample. In other cases, the Q and I signals are used directly.

As an alternative to using an electronic heterodyne downmixing system, it is also possible to reduce the frequency of detection using an optical heterodyne approach. Such an optical approach is disclosed in U.S. Pat. No. 5,408,327, incorporated herein by reference. In the latter system, both of the laser beams are modulated but at slightly different frequencies. Both beams generate thermal and plasma waves at their respective modulation frequencies. The beam from one laser picks up an intensity modulation upon reflection due to the modulated optical reflectivity induced in the sample by the other beam. The PMR signal picked up upon reflection "mixes" with the inherent modulation of the beam, creating additional modulations in the beam at both the sum and difference frequency. This process is analogous to electrical heterodyning. The difference or "beat" frequency is much lower than either of the initial beam modulation frequencies and can therefore be detected by a low frequency lock-in amplifier.

To insure proper repeatability of the measurements, the signals must be normalized in processor 1061 Accordingly, and as discussed in the above identified patents, in the preferred embodiment, a variety of reference detectors would be provided, the outputs of which are used to normalize the output of detector 126. Other optical elements, such as filters, collimators, shutters and steering optics would be included, all of which are all well known to those skilled in the art.

In some measurements, the two beams will be positioned so that the spots will overlap on the sample surface. In addition, measurements can be taken at various spacings between the pump and probe beam spots. Measurements at different spatial separations are discussed in greater detail in U.S. Pat. No. 5,978,074.

As noted above, there are many different thermal/plasma wave measurement techniques besides the measurement of modulated optical reflectivity. These devices are described in the above-cited patents and include measurement of the angular deviations of the probe beam as well as interferometric techniques.

Information about such systems can be found in U.S. Pat. Nos. 4,521,118; 5,522,510; 5,298,970; 6,411,390 and 6,268,916 all of which are incorporated herein by reference. Such systems for monitoring the variations of a probe beam are within the scope of the subject invention.

The pump beam generates both carrier plasma and thermal waves in a sample 114. Detector 126 measures the modulated reflectance, which is proportional to the nonradiative energy, produced by both the plasma and thermal waves. The modulated reflectance is described by the following equation:

$$\frac{\Delta R}{R} = \frac{1}{R}\left(\frac{\partial R}{\partial T}\Delta T_0 + \frac{\partial R}{\partial N}\Delta N_0\right)$$

where $\Delta T_0$ and $\Delta N_0$ are the temperature and the carrier plasma density at the surface of a semiconductor, R is the reflectance, dR/dT is the temperature reflectance coefficient and dR/dN is the carrier reflectance coefficient. For silicon, dR/dT is positive in the visible and near-UV part of the spectrum while dR/dN remains negative throughout the entire spectrum region of interest. This difference in signs decreases the total PMR signal due to partial compensation of changes in reflectance caused by the thermal and carrier plasma waves.

Fixed Wavelength Operation

Figure 2:
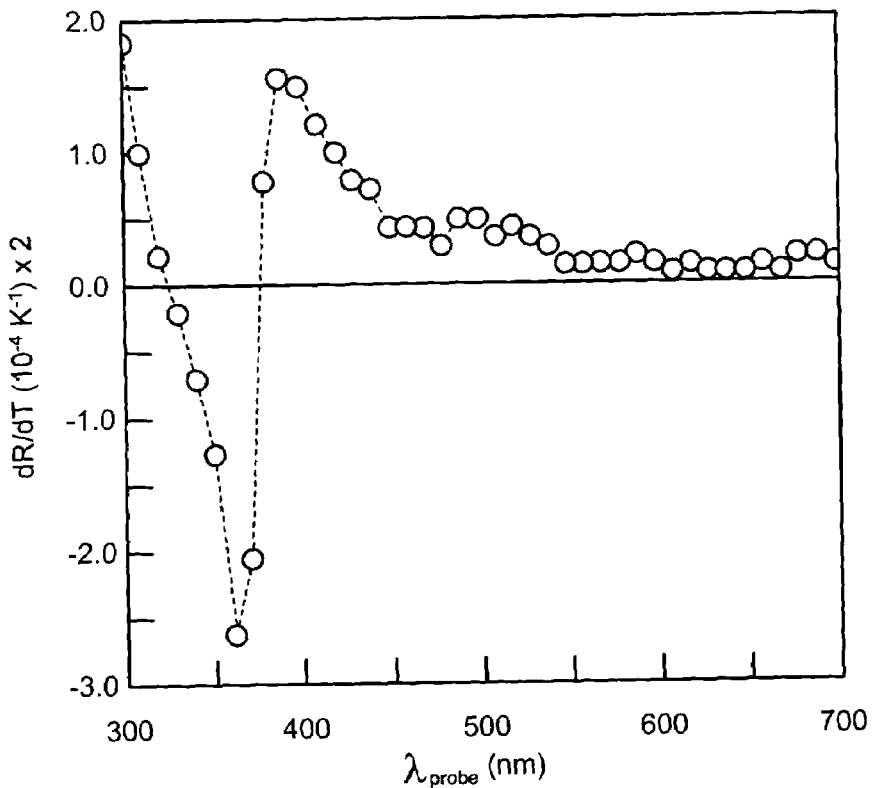
FIG. 2 is a graph showing the temperature reflectance coefficient of an idealized sample plotted as a function of measurement wavelength.

As shown in FIG. 2, dR/dT increases dramatically in the near-UV wavelength range 390–410 nm and decreases dramatically in the UV wavelength range around 360 nm. Although not shown, dR/dN remains practically unchanged over this range of wavelengths. For implementations where probe laser 104 operates at a fixed wavelength, the relationship between the dR/dT and dR/dN waveforms results in two desirable operating modes for modulated reflectance measurement system 100. For the first, probe laser 102 operates in the 400–405 nm wavelength range. At that spectral range, the difference between dR/dT and dR/dN increases the signal measured by detector 126 by as much as a factor of ten when compared to conventional PMR systems when measuring samples with thermally-dominated modulated reflectance signals.

For the second operating mode of modulated reflectance measurement system 100, probe laser 102 operates in the 360 nm wavelength range. At that spectral range, both the temperature and carrier plasma reflectance coefficients would be of the same (negative) sign leading to a constructive interference between the thermal and carrier plasma wave contributions to the total PMR signal. As a result, the overall PMR signal is expected to increase even more than one would anticipate from the increased thermal component (higher absolute value of dR/dT). This UV spectral region could be beneficial for almost all conventional TP applications including those where the signal is dominated by the carrier plasma effects, such as junction depth measurements in implanted and annealed semiconductors.

Tunable Wavelength Operation

With appropriate modifications, it is possible to configure modulated reflectance measurement system 100 to be wavelength tunable. For this type of configuration, probe laser 104 produces a probe beam at a nominal or central wavelength $\lambda_0$ within the UV spectrum. Probe laser 104 is tunable around $\lambda_0$ in order to be able to turn the thermal wave component of the PMR signal on and off and/or to maximize its amplitude.

Figure 3:
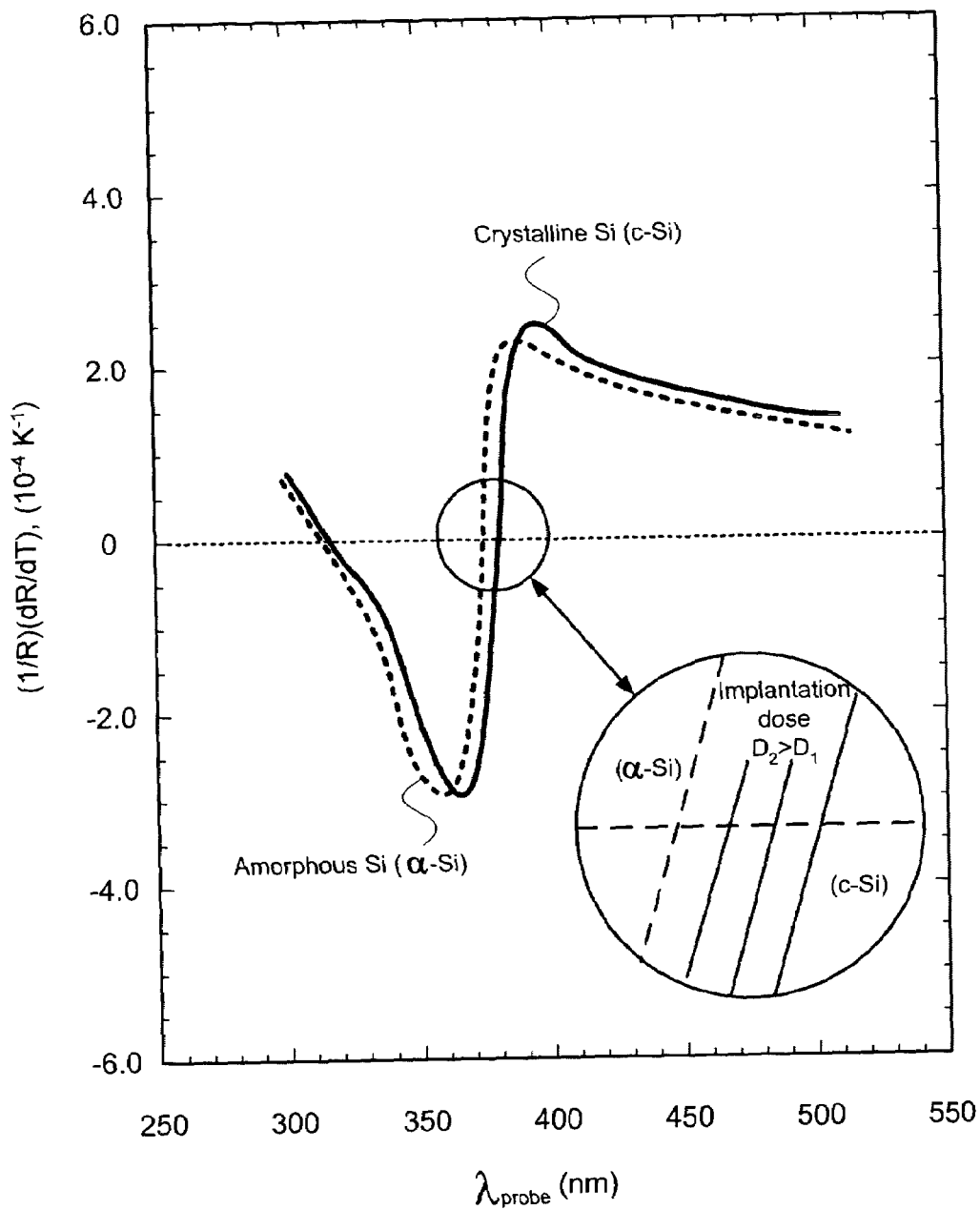
FIG. 3 is a graph showing the temperature reflectance coefficients of amorphous silicon and crystalline silicon plotted as a function of measurement wavelength.

As shown in FIG. 3, wavelength dependencies for the thermal reflection coefficients for the crystalline (c-Si) and amorphous (α-Si) silicon exhibit a nonmonotonic behavior in the near-UV and UV parts of the spectrum. In the spectral range between ~370 nm (negative maxima of dR/dT) and ~405 nm (positive maxima of dR/dT) both dependencies cross a zero line. At these inflection points the amplitude of the thermal wave component is equal to zero, i.e., is fully compensated. The insert in FIG. 3 shows schematically an enlarged view of a family of dR/dT curves corresponding to Si samples implanted with different doses ($D_1$ and $D_2$) near the zero line. With curves for α-Si (completely amorphous) and c-Si (non-implanted) being the two extreme cases, all measurement points corresponding to different samples with different implantation doses (or energies) will fall in between these two extremes.

In practical measurements, the probe beam wavelength is first tuned to compensate for the thermal wave component for the sample implanted with the first dose $D_1$. Then the second measurement of the sample with dose $D_2$ is taken at the same wavelength. If $D_1$ and $D_2$ are different, the thermal wave component will appear indicating differences in sample characteristics. The sensitivity to implantation dose in such compensation measurements can be significantly higher than that for the conventional TP methodology at any other probe beam wavelengths.

Figure 4:
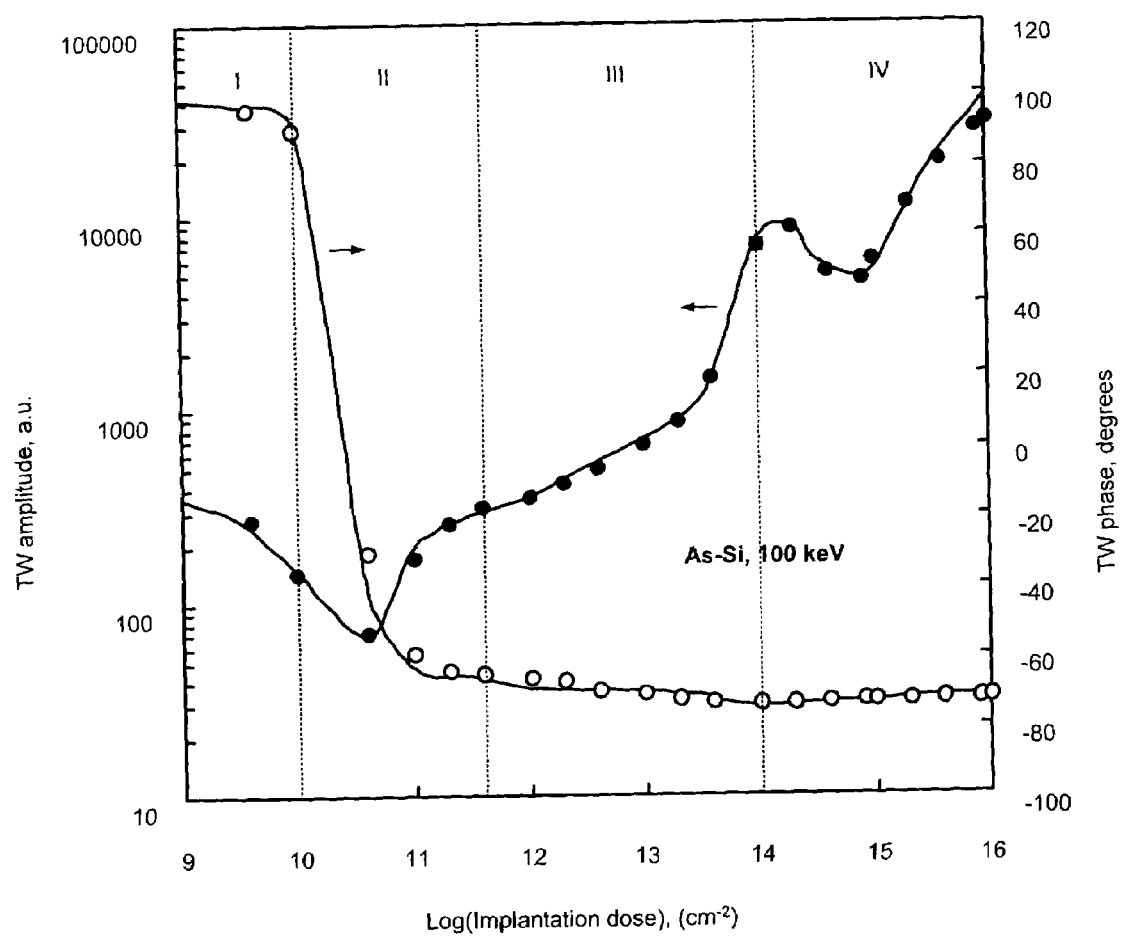
FIG. 4 is a graph plotting thermal wave amplitude and thermal wave phase as a function of implantation dose.

This compensation technique will be effective only for the samples exhibiting a thermally-dominated behavior of the PMR signal. Unfortunately, ion-implanted semiconductors do not always exhibit this type of behavior. FIG. 4 illustrates schematically a typical PMR signal amplitude (left scale) and phase (right scale) dose behavior. As can be appreciated, the PMR amplitude and phase dose dependencies exhibit different behavior in different parts of the dose spectrum depending on the physical mechanism dominating the PMR signal—thermal wave or carrier plasma.

Figure 5:
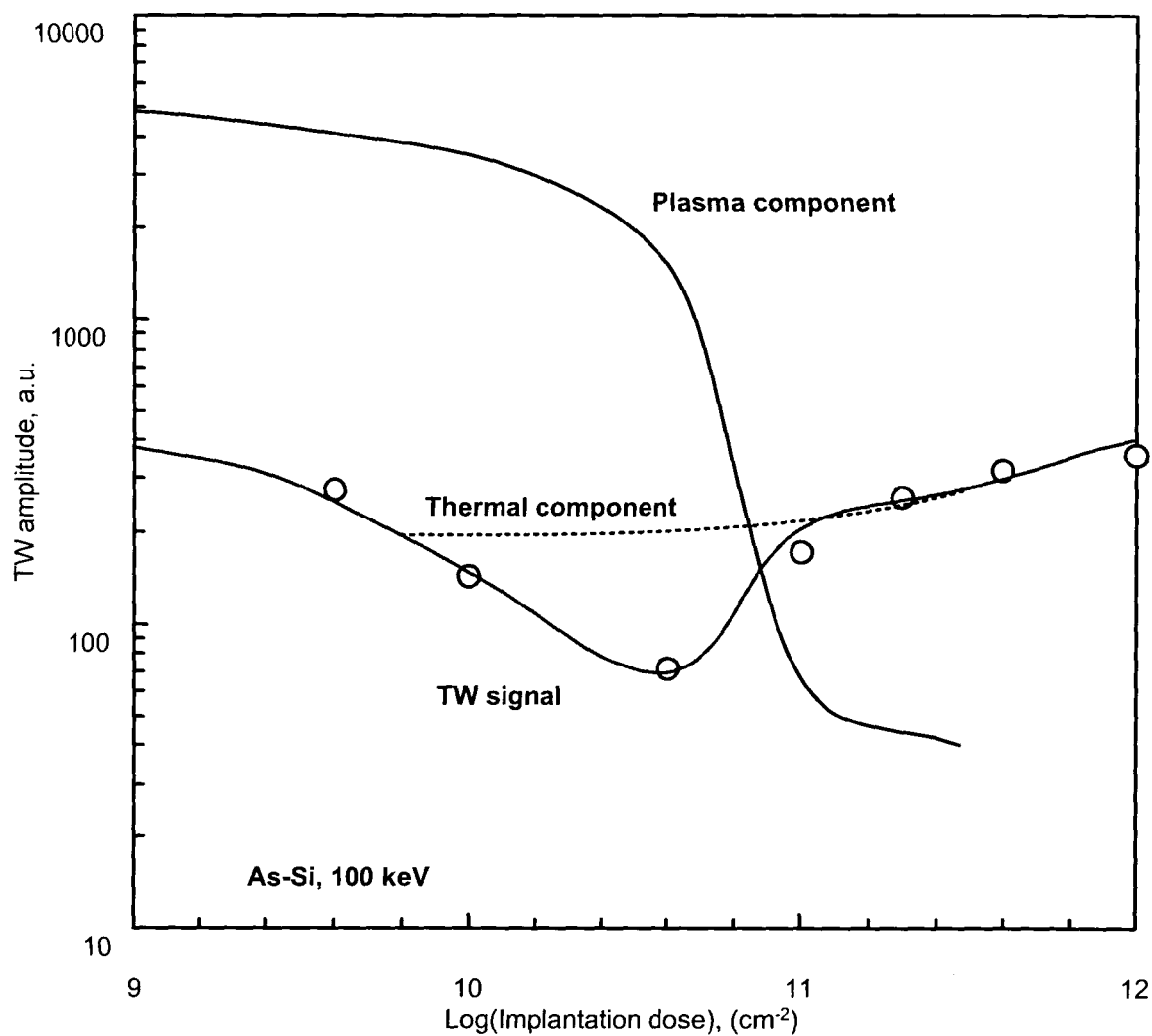
FIG. 5 is a detailed view of the plasma-to-thermal transition region originally shown in FIG. 4.

At low implantation doses (the region marked "I" in FIG. 4), the signal is plasma-dominated while at intermediate and high implantation doses (the regions "III" and "VI") thermal wave component dominates the signal. In the region marked "II", the amplitude of the carrier plasma wave component is commensurate with that of the thermal one and, being of the opposite sign for the set of the pump/probe beam wavelengths from the visible part of the spectrum, results in a sharp negative peak in a plasma-to-thermal transition region. In region II, the PMR phase experiences a sharp (near 180°) drop indicating a change in the dominant physical mechanism behind the PMR signal from plasma to thermal. Dynamics of the carrier plasma wave and thermal components of the TW signal in this region is shown in more details in FIG. 5.

As shown in FIG. 4, PMR phase is a sensitive parameter only in the plasma-to-thermal transition region (i.e., when the thermal wave and plasma component amplitudes are comparable) and carries almost no information outside this region. To take advantage of PMR phase sensitivity in the plasma-to-thermal transition region, modulated reflectance measurement system 100 is configured so that probe laser 104 is tunable in the UV to near-UV spectral range (370–410 nm). During measurement, this is used to equalize the contributions from the thermal wave and carrier plasma to the total PMR signal. This effectively shifts the dose position of this transition region by changing relative amplitudes of the carrier plasma and thermal wave components. As a result, it becomes possible to measure and analyze PMR phase information for a much broader range of dosages. In a photothermal system having more than two lasers it would then be possible to shift a very sensitive TW phase drop back and forth on implantation dose scale depending on the sample under investigation.

In general, it should be appreciated that the implementation of FIG. 1 is intended to be representative in nature. The use of UV probe lasers, both fixed and tunable is possible with a range of measurement systems and is not limited to the specific combination of components shown in FIG. 1.

The invention claimed is:

1. A method for evaluating a sample, the method comprising:
generating an intensity modulated pump beam;
generating a probe beam at a wavelength within the UV range that corresponds to a local maxima of the temperature reflectance coefficient of the sample;
focusing the pump beam on the sample to periodically excite a region of the sample surface;
focusing the probe beam within the periodically excited region;
monitoring a portion of the probe beam that is reflected by the periodically excited region and generating corresponding output signals; and
evaluating the sample by analyzing the detector output signals.

2. A method for evaluating a sample, the method comprising:
focusing an intensity modulated pump beam on the sample surface to periodically excite a first measurement site;
focusing an ultra-violet probe beam within the first measurement site;
measuring the modulation imparted to the probe beam by the first measurement site; and
tuning the wavelength of the probe beam to minimize the thermal wave contribution to the probe beam modulation.

3. A method as recited in claim 2 that further comprises the steps of:
focusing the pump beam on the sample surface to periodically excite a second measurement site;
focusing the ultra-violet probe beam within the second measurement site;
measuring the modulation imparted to the probe beam by the second measurement site; and
comparing the modulations imparted by the first and second measurement sites.

4. A method for evaluating a sample, the method comprising:
focusing an intensity modulated pump beam on the sample surface to periodically excite a first measurement site;
focusing an ultra-violet probe beam within the first measurement site;
measuring the modulation imparted to the probe beam by the first measurement site; and
tuning the wavelength of the probe beam to vary the thermal and plasma wave contributions to the probe beam modulation.

5. A method as recited in claim 4, wherein the wavelength of the probe beam is varied to equalize the thermal and plasma wave contributions to the probe beam modulation.

6. A device for evaluating a sample, the device comprising:
a first illumination source producing an intensity modulated pump beam for periodically exciting a region on the sample;
a second illumination source producing a single probe beam to reflect off the region on the sample surface that has been periodically excited where the probe beam has a spectral range selected from a group that includes: 395 to 410 nm and 355 to 365 nm;
optics for combining the pump and probe beams so that the pump and probe beams propagate collinearly to the sample;
a detector for monitoring the modulated changes in the power of the single reflected probe beam and generating output signals in response thereto, said output signals corresponding to the modulated optical reflectivity of the sample; and
a processor for evaluating the sample using the detector output signals.

7. A device as recited in claim 6, wherein the spectral range of the probe beam is 400 to 405 nm.

8. A device for evaluating a sample, the device comprising:
a first illumination source producing an intensity modulated beam for periodically exciting a region on the sample;
a second illumination source producing a probe beam to be reflected by the periodically excited region, where the probe beam has a wavelength within the UV range that corresponds to a local maxima of the temperature reflectance coefficient of the sample;
a detector for monitoring the modulated changes in the reflected probe beam and generating output signals in response thereto; and
a processor for evaluating the sample by analyzing the detector output signals.

9. A device for evaluating a sample, the device comprising:
a first illumination source producing an intensity modulated beam for periodically exciting a region on the sample;
a second illumination source producing a probe beam to be reflected by the periodically excited region, where the wavelength of the probe beam is tunable to minimize the thermal wave contribution to the probe beam modulation;

a detector for monitoring the modulated changes in the reflected probe beam and generating output signals in response thereto; and a processor for evaluating the sample by analyzing the detector output signals.

10. A device for evaluating a sample, the device comprising:

a first illumination source producing an intensity modulated beam for periodically exciting a region on the sample;

a second illumination source producing a probe beam to be reflected by the periodically excited region, where the wavelength of the probe beam is tunable to equalize the thermal and plasma wave contributions to the probe beam modulation;

a detector for monitoring the modulated changes in the reflected probe beam and generating output signals in response thereto; and a processor for evaluating the sample by analyzing the detector output signals.

11. A device for evaluating a sample, the device comprising:

a first illumination source producing an intensity modulated beam for periodically exciting a region on the sample;

a second illumination source producing a probe beam to be reflected by the periodically excited region, where the wavelength of the probe beam is tunable to vary the thermal and plasma wave contributions to the probe beam modulation;

a detector for monitoring the modulated changes in the reflected probe beam and generating output signals in response thereto; and a processor for evaluating the sample by analyzing the detector output signals.

* * * * *